(12) United States Patent
Tragut et al.

(10) Patent No.: US 6,387,222 B1
(45) Date of Patent: May 14, 2002

(54) CONTINUOUS ISOLATION OF A HIGH-MELTING MATERIAL BY DISTILLATION

(75) Inventors: Christian Tragut, Wachenheim; Gerd Kaibel, Lampertheim, both of (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 09/538,503

(22) Filed: Mar. 30, 2000

(30) Foreign Application Priority Data

Apr. 1, 1999 (DE) .......................... 199 14 966

(51) Int. Cl.$^7$ .............................. B01D 3/42; B01D 5/00; C07C 27/28; C07C 41/42
(52) U.S. Cl. .................... 203/2; 196/111; 202/160; 202/189; 203/3; 203/99; 203/DIG. 19; 203/47; 568/699; 568/913
(58) Field of Search .................. 202/158, 189, 202/160, 182, 202; 203/74–75, 77–78, 80, 99, DIG. 19, 2, 3, 47, 48; 62/630, 631; 196/111

(56) References Cited

U.S. PATENT DOCUMENTS

| | | | | |
|---|---|---|---|---|
| 3,607,671 A | * | 9/1971 | Riethmann et al. | 203/42 |
| 4,391,617 A | * | 7/1983 | Way | 55/82 |
| 4,419,188 A | * | 12/1983 | McCall | 203/84 |
| 4,460,396 A | * | 7/1984 | Kaiser et al. | 62/28 |
| 4,997,580 A | * | 3/1991 | Karydas et al. | 252/8.3 |
| 5,271,811 A | * | 12/1993 | Rittner et al. | 203/483 |
| 5,339,648 A | * | 8/1994 | Lockett et al. | 62/24 |
| 5,411,707 A | * | 5/1995 | Hiatt | 422/68.1 |
| 5,660,690 A | * | 8/1997 | Gornowicz et al. | 203/1 |
| 5,914,012 A | * | 6/1999 | Kaibel et al. | 202/158 |
| 5,970,742 A | * | 10/1999 | Agrawal et al. | 62/630 |
| 6,106,674 A | * | 8/2000 | Agrawal et al. | 203/75 |

FOREIGN PATENT DOCUMENTS

| | | |
|---|---|---|
| CA | 1242309 | 7/1984 |
| CA | 12222717 | 7/1984 |
| EP | 122367 | 10/1984 |
| EP | 126288 | 11/1984 |
| EP | 133510 | 2/1985 |

* cited by examiner

Primary Examiner—Virginia Manoharan
(74) Attorney, Agent, or Firm—Keil & Weinkauf

(57) ABSTRACT

A method of distillation for separating a material which is solid at ambient temperature from a lower boiling and lower melting point material, and the apparatus.

11 Claims, 4 Drawing Sheets

CONTINUOUS ISOLATION OF A HIGH-MELTING MATERIAL BY DISTILLATION

The present invention relates to a process for the continuous separation of a relatively high-melting material from a starting mixture comprising a relatively high-melting material and a low-melting low boiler by distillation and a distillation apparatus for carrying out the process.

In general, not only the low boiler and the relatively high-melting material but also further components are present in such a starting mixture. The relatively high-melting material is usually to be isolated as intermediate high-boiling desired product from the starting mixture. In the customary purification of intermediate-boiling desired products by distillation to remove low- and high-boiling impurities, various process variants are customarily employed. In the simplest case, the feed mixture comprising the relatively high-melting material is separated into two fractions, namely a low-boiling top fraction and a high-boiling bottom fraction. In the separation of feed mixtures into more than two fractions, for example into low boilers, intermediate boilers and high boilers, two or more distillation columns have to be used for this process variant. In order to limit the outlay in terms of apparatus, the fractionation of multicomponent mixtures which consist of more than two components is also carried out using components which are suitable for taking off liquid or gaseous media at the side. However, the opportunities for using distillation columns with side offtakes are greatly restricted by the fact that the products taken off at the side offtakes are normally not completely pure. Products taken off at the side from the enrichment section of a distillation apparatus, which are usually in liquid form, contain proportions of low-boiling components which are normally separated off at the top. A similar situation applies to products taken off at the side in the stripping section, which are usually in vapor form and the side products contain proportions of the high boiler. When using such conventional side offtake columns, contaminated side products are virtually always obtained, so that the use of side offtake columns is unsuitable for isolating pure materials. Particularly for isolating intermediate-boiling pure materials from multicomponent mixtures, it is therefore generally necessary to use column arrangements which consist of at least two separate columns.

An advantageous alternative is given by dividing wall columns or thermally coupled distillation columns. The use of dividing wall columns makes it possible to isolate side products, i.e. intermediate-boiling components, in pure form from multicomponent mixtures. In the case of dividing wall columns, a dividing wall is installed in the middle region. This extends to above and below the feed point. On the other side opposite the feed point, there is a side offtake. The dividing wall is thus located between the side offtake and the feed point. In the column region which is divided by the dividing wall, transverse mixing of liquid and vapor streams is not possible. This reduces the total number of distillation columns required in the fractionation of multicomponent mixtures. This type of column is in principle a constructional simplification of thermally coupled distillation columns, but the latter involve higher capital costs. Compared to a combination of conventional distillation columns, dividing wall columns and thermally coupled columns offer advantages both in respect of energy consumption and capital costs, and are therefore preferably used in the industry. Information on dividing wall columns and thermally coupled distillation columns is given in EP-A-0 122 367, EP-B-0 126 288 and EP-B-0 133 510.

The fractional distillation of a multicomponent mixture which comprises an intermediate-boiling component having a melting point above ambient temperature is more complicated technically. In such a case, it is not readily possible to remove the heat of condensation at the top of one column by means of a cooler or by means of a condenser supplied with cooling water or backcooling water. The heat exchanger, i.e. an air cooler or a cooler operated using cooling water or backcooling water, would in such a case quickly become coated with crystals since the component having the high melting point would deposit. Such a crystal layer on a condenser is disadvantageous, since heat transfer is reduced and the condenser can therefore no longer fulfill its function as desired.

As a possible remedy, it is possible to employ a combination of two or more condensers which are alternated between the cooling mode and a phase in which the solid deposits are remelted and removed. This method of operation is complicated and requires a high level of automation.

The use of a secondary medium is widespread in the industry. Examples of suitable secondary media are thermostatted oil or hot water. The temperature of the secondary medium is set so that crystal formation on the heat exchanger surfaces is prevented. In general, such a secondary medium is in contact with a further cooling medium to which the heat can be transferred. Thus, two cooling circuits are required and this incurs increased capital costs.

A further disadvantage is blockages caused by the relatively high-melting component: the latter can, if it is not deposited on the condenser, deposit in down-stream waste gas lines. This causes undesirable pressure drops.

It is an object of the present invention to devise a process by means of which a relatively high-melting material, i.e. a relatively high-melting component, can be isolated from a starting mixture comprising a plurality of components. In this process, no solid should be deposited on the corresponding condenser used in the distillation. In addition, the high-melting material should be isolated from the corresponding starting mixture by means of an effective and energetically advantageous distillation process.

The achievement of this object starts out from a process for the continuous separation of a relatively high-melting material from a starting mixture comprising the relatively high-melting material and a low-melting low boiler, where the low boiler consists of one or more components having a boiling point lower than that of the relatively high-melting material, by distillation in a distillation apparatus configured either as a dividing wall column or as a system of thermally coupled distillation columns. The object of the invention is achieved by the distillation apparatus being fitted with a condenser located at the top above the offtake point for the relatively high-melting material, where that part of the surface of this condenser which is in contact with the interior of the distillation apparatus has a temperature lower than the melting point of the relatively high-melting material and the concentration of the low boiler at the top becomes so high that no deposition of the relatively high-melting material occurs in the condenser.

In this context, "no deposition" of the relatively high-melting material means that less than 1% by weight, preferably less than 0.001% by weight, of the relatively high-melting material fed into the column is deposited in solid form in the condenser. For the purposes of the present invention, a relatively high-melting material is a material which has a melting point higher than the average temperature prevailing on the surface of the condenser used. Conversely, a low-melting material has a melting point below the mean surface temperature of the condenser. Thus, a low-melting material cannot deposit as a solid on such a condenser. Low-melting and relatively high-melting are therefore relative properties. Depending on the distillation process, i.e. depending on the surface temperature of the condenser employed, the same material can be relatively high-melting or low-melting.

The present invention also provides a distillation apparatus which is configured either as a dividing wall column or as a system of thermally coupled distillation columns for carrying out the above process. In the distillation apparatus, a condenser is located at the top above an offtake point for an intermediate-boiling, relatively high-melting material, where that part of the surface of the condenser which is in contact with the interior of the dividing wall column or the interior of the system of thermally coupled distillation columns has a temperature lower than the melting point of the intermediate-boiling, relatively high-melting material and the process conditions are such that the concentration of a low boiler present in the dividing wall column or in the system of thermally coupled distillation columns in addition to the intermediate-boiling, relatively high-melting material becomes so high at the top that no deposition of the intermediate-boiling, relatively high-melting material occurs in the condenser.

For the purposes of the present invention, process conditions are the concentrations of the materials present in the distillation apparatus, the introduction and taking-off of the materials, the surface temperature of the condenser, the pressures and temperatures prevailing at the various points of the distillation apparatus and the type and number of theoretical plates in the distillation apparatus.

The distillation apparatus preferably has only one condenser. This is located in the top section of the column, above the offtake point for the relatively high-melting material. In the case of a dividing wall column, the offtake point for the relatively high-melting material is generally below the upper end of the dividing wall. In the case of thermally coupled distillation columns, the offtake point for the relatively high-melting material is not located in the column into which the starting mixture is introduced, but in a second column. The latter is connected by connecting lines to the column into which the starting mixture is introduced. In the case of thermally coupled distillation columns, the offtake point for the relatively high-melting material is also located below the condenser. This means that in this case the condenser is located above the point at which the uppermost connecting line between the two coupled columns is connected to the column having the condenser.

In a preferred embodiment, the starting mixture comprises not only the relatively high-melting material and the low boiler but also a high boiler consisting of one or more components, where all components of the high boiler have a boiling point higher than that of the relatively high-melting material. In such a case, the relatively high-melting material is an intermediate boiler which is present in addition to low boilers and high boilers in the starting mixture. In principle, the starting mixture can further comprise, in addition to low boilers, high boilers and the relatively high-melting material, other constituents which are usually either not distilled or have a boiling point similar to that of the relatively high-melting material. The relatively high-melting material is generally the desired product from the fractional distillation and is, if a dividing wall column is used, obtained as side-offtake product.

In general, only part of the low boiler in the starting mixture is present as foreign substance, i.e. as additional component added purely for the purpose of the fractional distillation. This means, for example, that when low-boiling impurities are present in the crude relatively high-melting material, the addition of further low boilers, referred to above as foreign substances, can be reduced. If the impurities functioning as low boilers are present in a sufficient concentration, no further low boiler (foreign substance) has to be added to the starting mixture. Not using foreign substances as process engineering additives is of great advantage, since the latter have to be separated off again afterwards. The associated, additional separation required has an adverse effect on the economics of the process concerned.

Suitable relatively high-melting materials in the process of the present invention are, for example, isomers of dimethylhexanediol. As low boiler, it is possible to use low-boiling alcohols and/or low-boiling aromatic hydrocarbons and/or low-boiling ethers.

In general, the distillation apparatus is configured either as a packed column containing random packing elements or ordered packing or as a tray column. It is frequently advisable, particularly if the substances to be separated are thermally sensitive and have low boiling points, to carry out the distillation under reduced pressure. In such a case (for example in the distillation of dimethylhexanediol, which is preferably carried out at a pressure of from 50 to 300 mbar), low pressure drop packed columns are advantageous. Here, ordered mesh packing having a specific surface area of from 200 to 800 $m^2/m^3$, preferably from 400 to 600 $m^2/m^3$, is advantageous.

The low boiler can function as solvent for the relatively high-melting material. Crystals of the relatively high-melting material which deposit in the condenser are then continually dissolved by the low boiler and thereby removed from the condenser. A further possibility is that the low boiler reduces the melting point of the relatively high-melting material, for example by formation of a eutectic mixture. If the concentration of the low boiler in the region of the condenser is too low, the above effects are not sufficient to prevent deposition of the relatively high-melting material in the condenser.

In a preferred embodiment, the necessary increase in concentration of the low boiler at the top is achieved by a) a sufficiently high number of theoretical plates in the upper region of the distillation apparatus and/or b) sufficient heating of the distillation apparatus and/or c) controlling the amount of low boiler taken off at the top.

In the present context, the upper region of the distillation apparatus is, in the case of a dividing wall column, the region above the dividing wall, while in the case of a system of thermally coupled distillation columns it is the region above the point at which the uppermost connecting line between the two coupled columns is connected to the column having the condenser.

In general, the increase in concentration of the low boiler at the top is controlled by regulating the temperature in the upper region of the distillation apparatus. To ensure sufficient amounts of low boiler in the top section of the distillation apparatus or to avoid deposition of the relatively high-melting material in the condenser, one or more items of the following regulation concept have been found to be particularly useful:

A temperature control using the outflow, the reflux ratio or preferably the runback flow as adjustment parameter is installed in the upper region of the distillation apparatus; this temperature control can be supplemented so that if the set temperature is exceeded and at the same time the adjustment parameter corresponds to an infinitely high reflux ratio, additional low boiler is introduced at the top of the column.

A temperature control using the amount taken off at the bottom as adjustment parameter is installed in the region of the bottom.

If a dividing wall column is used as distillation apparatus, the rising stream of vapor on the two side of the dividing wall is divided in a ratio of from 0.8:1.2 (v/v) to 1.2:0.8 (v/v).

To take off the relatively high-melting material at the side offtake, both internal collection spaces and collection spaces located outside the column are suitable. These generally assume the function of a pump reservoir or in each case ensure a sufficiently high static liquid height. The latter achieves an onward liquid flow regulated by means of regulating devices, for examples valves.

DETAILED DESCRIPTION OF DRAWINGS

Figure 1:
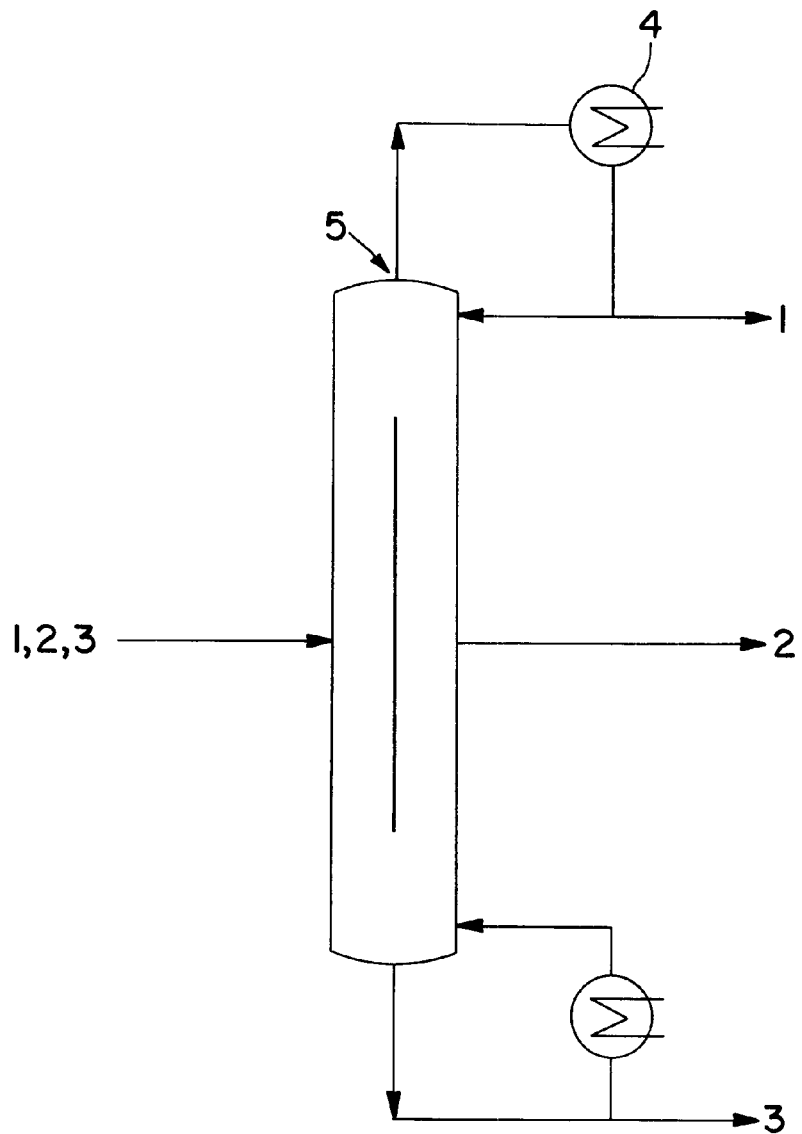
FIG. 1 schematically shows a dividing wall column and FIG. 2, FIG. 3 and FIG. 4 schematically show systems of thermally coupled distillation columns.
Figure 2A:
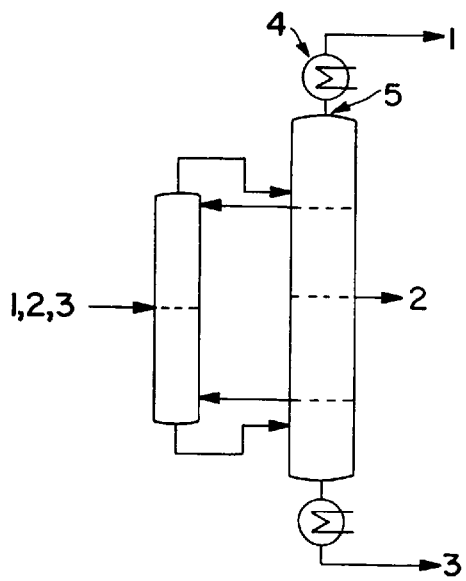
Figure 2B:
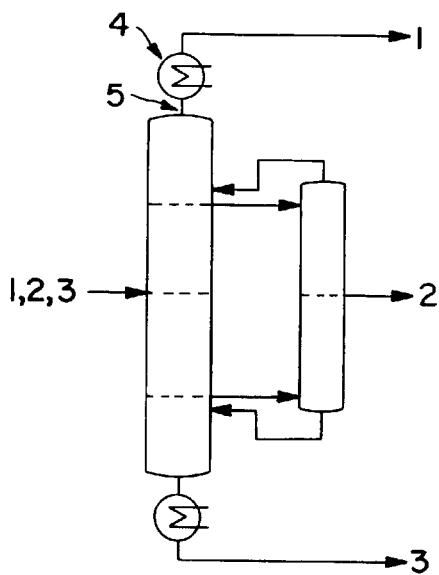
Figure 2C:
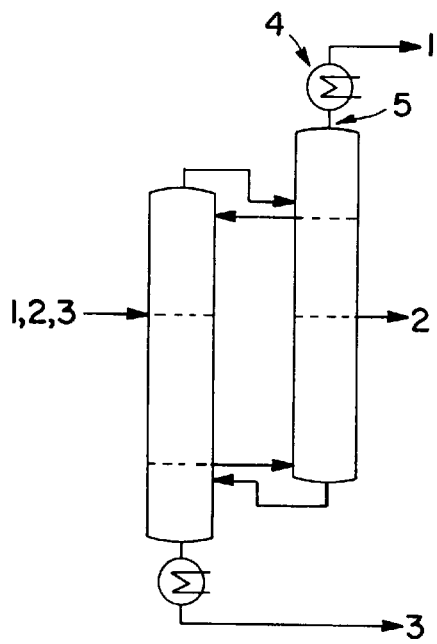
Figure 2D:
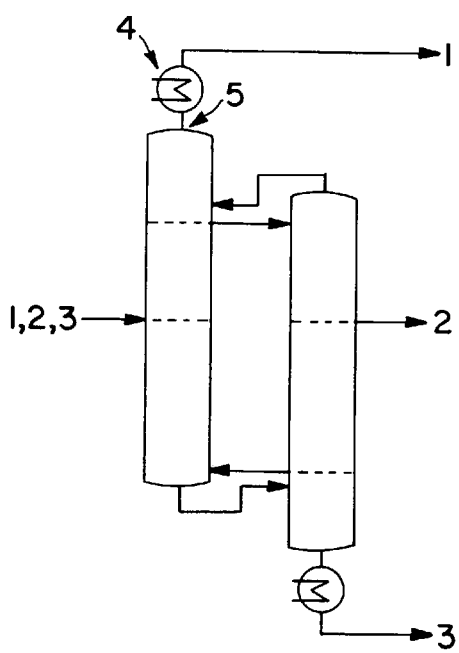
Figure 3A:
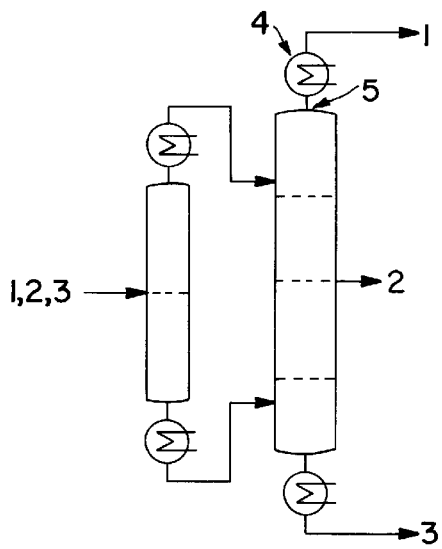
Figure 3B:
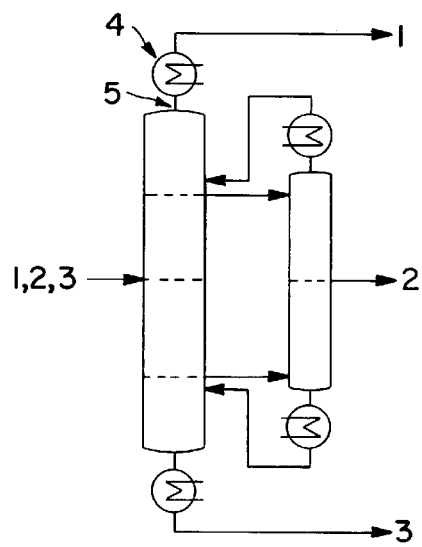
Figure 3C:
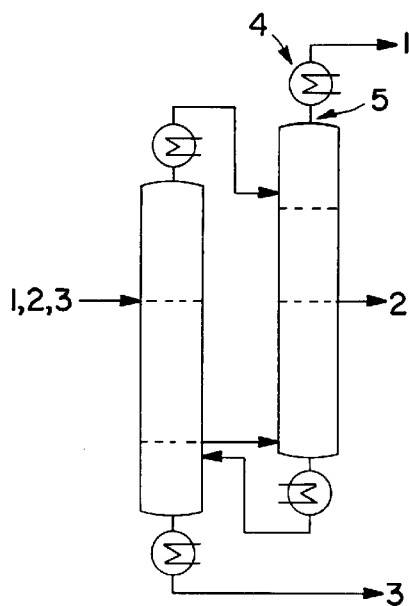
Figure 3D:
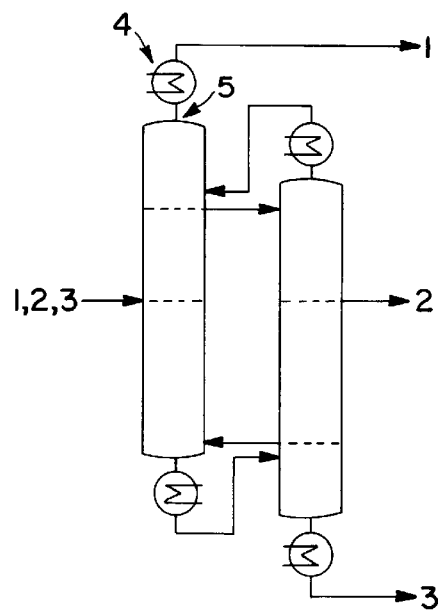
Figure 4A:
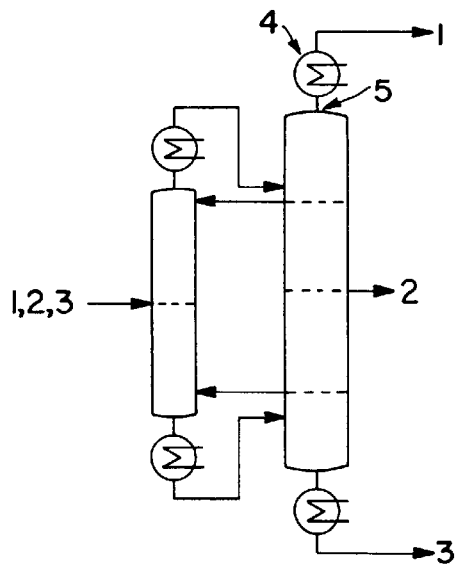
Figure 4B:
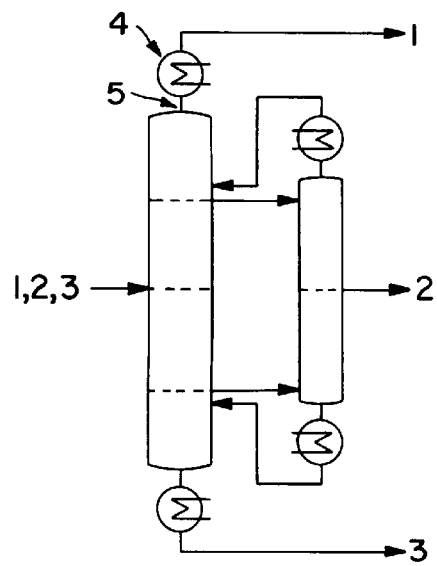
Figure 4C:
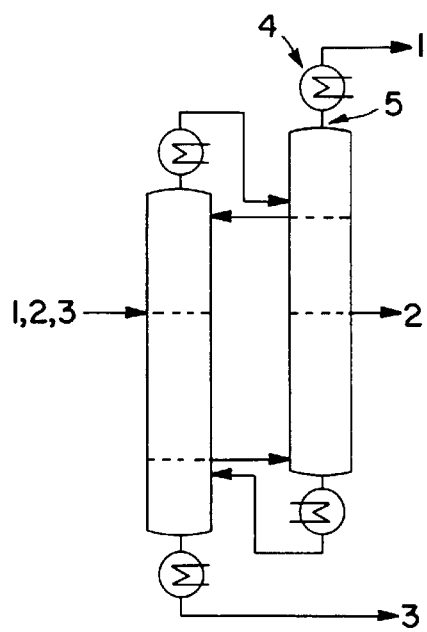
Figure 4D:
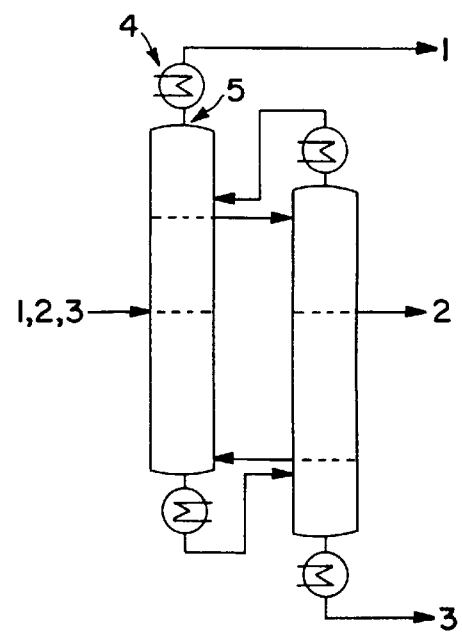

FIGS. 1 to 4 show the fractionation of a multicomponent mixture. When applied to the process of the present invention, I would be low boilers, 2 would be the relatively high-melting material (as intermediate boiler) and 3 would be high boilers. The intermediate boiler, i.e. the relatively high-melting material 2, is obtained in pure form.

Reference No. 4 is the condenser at the top of the distilling apparatus and Reference No. 5 is the part of the condenser in which is in contact with the interior of the distilling apparatus. This part is the region where the pipe which connects the distilling apparatus with the condenser meets the distilling apparatus.

The invention is illustrated below by means of examples:

EXAMPLE 1

The distillation was carried out by means of laboratory column having an internal diameter of 50 mm. The middle section of the column was divided into two symmetrical parts by a dividing wall. The undivided section of the column, below the dividing wall, had a packing height of 30 cm and was filled with mesh packing (surface area: 1200 $m^2/m^3$). The middle, divided region of the column (height: 90 cm) was filled with wire rings (diameter: 3 mm) on both sides of the dividing wall. Above the middle section of the column, a swiveling funnel which divided the liquid stream in a division ratio of feed side to offtake side of 3:7 (v/v) was installed. The swiveling funnel, which is in principle located on top of the dividing wall, enables the inflow areas of the regions divided by the dividing wall to be varied—the swiveling funnel thus has the function of a "flap" which divides the liquid flow into the two regions. The undivided section of the column above the dividing wall (height: 60 cm) was provided with mesh packing (1200 $m^2/m^3$).

The distillation was carried out at a pressure at the top of 200 mbar. The temperature at the bottom was regulated to 185° C. by means of the amount taken off at the bottom. The temperature to which the bottoms were heated were 205° C. The amount taken off at the side was set by regulation of the level of the bottoms. The reflux ratio was set by regulation of the temperature in the middle of the upper region of the column. The feed flow was set to 150 g/h. The control temperature in the upper part of the column was 120° C. A total of 3567 g of a mixture comprising 60% by weight of isobutanol, 13% by weight of o-xylene, 13% by weight of 2,5-dimethylhexane -2,5-diol and 8% by weight of water were fed in. The relatively high-melting, intermediate-boiling material 2 was 2,5-dimethylhexane-2,5-diol. In addition, various trace components, mainly condensation products of acetone, were present in the feed mixture. At the top, 3117 g of a low boiler 1, namely a mixture having a residual 2,5-dimethylhexane-2,5-diol content of 0.04% by weight, were obtained. At the side offtake, 476 g of 2,5-dimethylhexane-2,5-diol having a purity of 99.72% by weight were obtained. At the bottom, only very little high boiler 3 was obtained. The relatively high-melting material 2 (2,5-dimethylhexane-2,5-diol) was not deposited as a solid at any point of the column used.

EXAMPLE 2

The experiment was carried out using a method analogous to Example 1.

The feed flow was set to 150 g/h. The temperature at the bottom was 202° C. The feed mixture comprised: 30% by weight of isobutanol, 23.8% by weight of 2,5-dimethylhexane -2,5-diol, 34% by weight of o-xylene, 2% by weight of methylbutanol and 8% by weight of water. The relatively high-melting, intermediate-boiling material 2 was 2,5-dimethylhexane-2,5-diol. In addition, various trace components, mainly condensation products of acetone, were present in the feed mixture. At the top, 2636 g of low boiler 1 (2,5-dimethylhexane-2,5-diol content about 2.2% by weight) were taken off. At the side offtake, 764 g of 2,5-dimethylhexane-2,5-diol having a purity of 99.9% by weight were obtained. At the bottom, 11 g of high boiler 3 having a content of 17.1% by weight were taken off during the time of the experiment. The relatively high-melting material 2 (2,5-dimethylhexane-2,5-diol) was not deposited as a solid at any point of the column used.

We claim:

1. In a continuous distillation process for the separation of a higher boiling material from a lower boiling material from an admixture thereof by vaporization and condensation utilizing a distillation apparatus, wherein the higher boiling material comprises a material which is solid at ambient temperature, wherein the lower boiling material comprises at least one material which has a lower melting point than the higher boiling material which is solid at ambient temperatures, wherein the distillation apparatus is a dividing wall distillation column or is a system of thermally coupled distillation columns, and wherein the distillation apparatus includes at least two offtake points, one for the higher boiling materials and above that, one for the lower boiling materials, the improvement wherein the admixture of higher boiling material and lower boiling material is fed into the distilling apparatus which is fitted with a condenser at the top of the distilling apparatus and above the offtake point for the higher boiling materials, a part of which condenser is in contact with the interior of the distilling apparatus, the temperature of that part of the condenser which is in contact with the interior of the distilling apparatus is controlled during distillation such that its temperature is lower than the melting point of the material which is solid at ambient temperature and the concentration of the lower boiling material in the upper portion of the distillation apparatus is kept sufficiently high such that there is substantially no deposition in the distillation apparatus of the said material which is solid at ambient temperature.

2. The process of claim 1 wherein the admixture includes at least one other high boiling material which has a boiling point higher than that of the material which is solid at ambient temperature.

3. The process of claim 1 wherein the condenser is the sole condenser of the distilling apparatus.

4. The process of claim 1 wherein the concentration of the lower boiling material in the upper portion of the distillation apparatus is achieved by
   a) a sufficiently high number of theoretical plates in the upper region of the distillation apparatus and/or
   b) sufficient heating of the distillation apparatus and/or
   c) controlling the amount of the lower boiling material taken off the top.

5. The process of claim 1 wherein part of the lower boiling material is a foreign substance.

6. The process of claim 1 wherein no foreign substance is present as a low boiling material.

7. The process of claim 1 wherein the distillation apparatus is configured as a packed column, containing either random or ordered packing, or as a tray column.

8. The process of claim 1 wherein the lower boiling materials comprise low boiling alcohols and/or low boiling ethers.

9. The process of claim 1 wherein the higher boiling material, which is solid at ambient temperature, comprises 2,5-dimethylhexane-2,5-diol.

10. In a distillation apparatus for the separation of a higher boiling material from a lower boiling material,
   wherein the higher boiling material comprises a material which is solid at ambient temperature,
   wherein the lower boiling material comprises at least one material which has a lower melting point than the higher boiling material which is solid at ambient temperatures,
   wherein the distillation apparatus is a dividing wall distillation column or a system of thermally coupled distillation columns,
   wherein the distillation apparatus includes at least two offtake points, one for the higher boiling materials and above that, one for the lower boiling materials,
   the improvement wherein
   the distilling apparatus is fitted with a condenser at the top of the distilling apparatus and above the offtake point for the higher boiling materials, a part of which condenser is in contact with the interior of the distilling apparatus, which apparatus includes a means for controlling the temperature of that part of the condenser which is in contact with the interior of the distilling apparatus during distillation such that its temperature is lower than the melting point of the material which is solid at ambient temperature and
   a means for maintaining the concentration of the lower boiling material in the upper portion of the distillation apparatus sufficiently high such that there is substantially no deposition in the distillation apparatus of the said material which is solid at ambient temperature.

11. The apparatus of claim 10 wherein the distilling apparatus is fitted with only one condenser.

* * * * *